(12) United States Patent
Teh

(10) Patent No.: US 12,137,877 B2
(45) Date of Patent: Nov. 12, 2024

(54) ENDOSCOPIC-RELEASE SURGICAL RETRACTOR

(71) Applicant: Kok Kheng Teh, Selangor (MY)

(72) Inventor: Kok Kheng Teh, Selangor (MY)

( * ) Notice: Subject to any disclaimer, the term of this patent is extended or adjusted under 35 U.S.C. 154(b) by 365 days.

(21) Appl. No.: 17/623,646

(22) PCT Filed: Jun. 24, 2020

(86) PCT No.: PCT/IB2020/055946
§ 371 (c)(1),
(2) Date: Dec. 29, 2021

(87) PCT Pub. No.: WO2021/005440
PCT Pub. Date: Jan. 14, 2021

(65) Prior Publication Data
US 2022/0249080 A1 Aug. 11, 2022

(30) Foreign Application Priority Data
Jul. 11, 2019 (MY) .............................. PI2019004024

(51) Int. Cl.
| *A61B 1/00* | (2006.01) |
| *A61B 17/02* | (2006.01) |
| *A61B 17/32* | (2006.01) |
| *A61B 1/317* | (2006.01) |

(52) U.S. Cl.
CPC .......... *A61B 1/00147* (2013.01); *A61B 17/02* (2013.01); *A61B 17/320036* (2013.01); *A61B 1/317* (2013.01)

(58) Field of Classification Search
CPC . A61B 17/02; A61B 17/0218; A61B 17/0281; A61B 17/320036
See application file for complete search history.

(56) References Cited

U.S. PATENT DOCUMENTS

| 659,182 | A | * | 10/1900 | Pilling | A61B 17/02 600/226 |
| 2,829,649 | A | * | 4/1958 | Glenner | A61B 17/42 600/210 |
| 4,306,547 | A | * | 12/1981 | Lowell | A61B 1/07 128/200.26 |
| 4,982,729 | A | * | 1/1991 | Wu | A61B 1/267 600/187 |
| 5,273,024 | A | | 12/1993 | Menon | |
| 5,402,771 | A | * | 4/1995 | Pilling | A61B 1/267 600/188 |
| 5,846,192 | A | * | 12/1998 | Teixido | A61B 17/02 600/210 |
| 6,007,487 | A | * | 12/1999 | Foley | A61B 17/3417 600/210 |
| 6,033,361 | A | | 3/2000 | Co | |

(Continued)

*Primary Examiner* — Nicholas W Woodall
(74) *Attorney, Agent, or Firm* — Renner, Kenner, Greive, Bobak, Taylor & Weber

(57) ABSTRACT

This invention relates to an endoscopic-release surgical retractor (1) comprising a blade (2) having an arch-shaped cross section and a handle (3) extending upwardly from the proximal end of the blade. The handle (3) is adapted to removably receive an L-shaped endoscope-retainer (5). The vertical arm (52) of the endoscope-retainer is adapted to receive an endoscope such that in use the endoscope is retained at the apex of the arch of the blade.

10 Claims, 8 Drawing Sheets

(56) References Cited

U.S. PATENT DOCUMENTS

| | | | | |
|---|---|---|---|---|
| 6,090,040 A | * | 7/2000 | Metro | A61M 16/0493 |
| | | | | 600/199 |
| 7,951,077 B2 | * | 5/2011 | Sayeg | A61B 17/02 |
| | | | | 600/210 |
| 10,349,823 B2 | * | 7/2019 | Opperman | A61B 1/00101 |
| 10,660,632 B2 | * | 5/2020 | Torrie | A61B 17/025 |
| 2006/0030756 A1 | | 2/2006 | Usher | |
| 2007/0288043 A1 | | 12/2007 | Rehnke | |
| 2013/0211201 A1 | * | 8/2013 | Wongsiri | A61B 1/32 |
| | | | | 600/245 |
| 2013/0345515 A1 | | 12/2013 | Fitzmaurice | |
| 2017/0020494 A1 | * | 1/2017 | Ross | A61B 18/148 |

\* cited by examiner

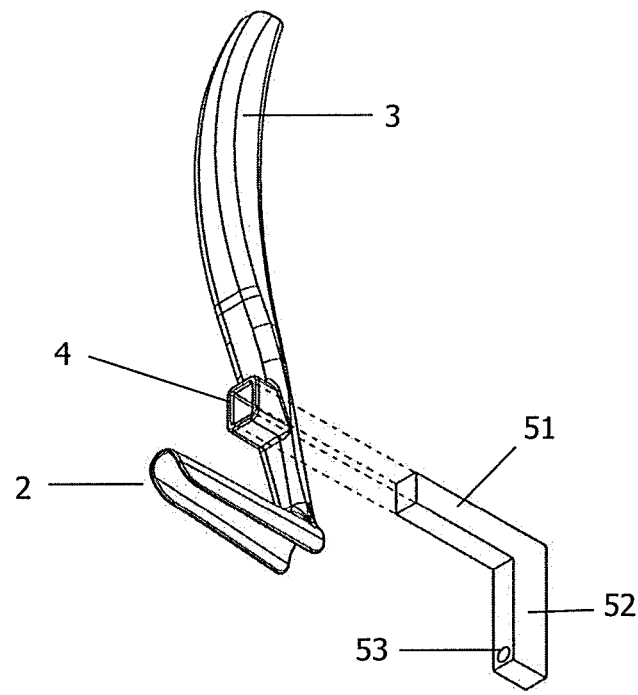
FIGURE 9
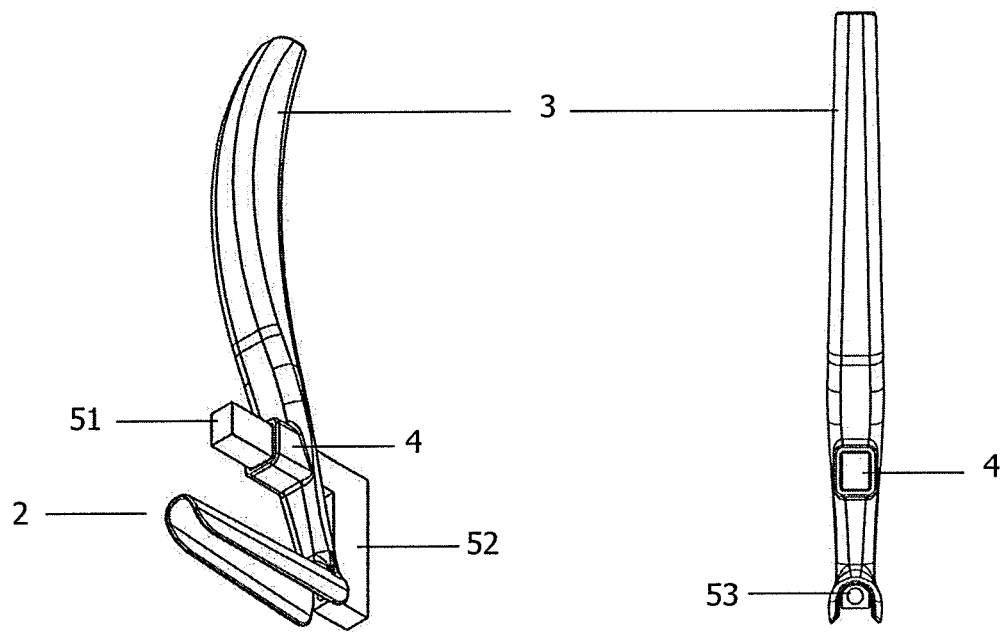
FIGURE 10
FIGURE 11

ENDOSCOPIC-RELEASE SURGICAL RETRACTOR

FIELD OF THE INVENTION

This invention generally relates to a surgical retractor for use in endoscopic release surgery.

DESCRIPTION OF THE PRIOR ART

An endoscopic release surgery is a procedure used to relieve discomfort associated with nerve compression syndrome or to treat various musculoskeletal conditions.

Nerve compression syndrome is a medical condition caused by direct pressure on a nerve. It normally causes symptoms such as pain, tingling, numbness and muscle weakness. Common nerve compression syndromes include carpal tunnel syndrome, plantar fasciitis, cubital tunnel syndrome and tarsal tunnel syndrome.

Carpal tunnel is a narrow passageway on the palm side of your wrist made up of bones and ligaments. The median nerve, which controls sensation and movement in the thumb and first three fingers, runs through this passageway along with tendons to the fingers and thumb. Carpal tunnel syndrome (CTS) is a medical condition when the median nerve is squeezed or compressed, causing pain, numbness, and tingling in the hand and arm. Over time, if the pressure on the median nerve continues untreated, it can lead to nerve damage and worsening symptoms. To prevent permanent damage, surgery to release the pressure on the median nerve may be necessary for some patients.

Conventionally, CTS can be treated with an Open Carpal Tunnel Release (OCTR) surgery, where an incision up to 5 cm is made in the vertical direction at the base of the palm of the hand to allow a surgeon to cut the transverse carpal ligament which consequently releases pressure on the median nerve and relieves the symptoms of carpal tunnel syndrome. After the ligament is cut, the skin is closed with stitches. During the OCTR surgery, there is a risk that the median nerve or other tissues may be damaged. Added to that, when the incision heals, there is extensive scar tissue which is both unsightly and painful and may impair full recovery of hand function.

Alternatively, CTS can also be treated with an Endoscopic Carpal Tunnel Release (ECTR) surgery using a thin tube with an endoscope that enables a surgeon to see the structures of the carpal tunnel without opening the entire area with a large incision. The ECTR surgery can be carried out using a single-portal technique (also known as Agee technique) where one thin tube, consisting of both the endoscope and a cutting tool, is guided through a small incision in the wrist, or using a two-portals technique (also known as Chow technique) where two small incisions are made in the wrist and palm. An endoscope is inserted through the small incision at the palm to view the carpal tunnel and the transverse carpal ligament is cut through another small incision at the wrist to release pressure on the median nerve.

ECTR surgery has been proven to have a shorter recovery time and the regaining of more complete hand strength compared to OCTR. However, ECTR surgery is associated with a higher risk of transient median nerve dysfunction attributed to surgical manipulation when inserting instruments into the stenotic carpal tunnel.

In light of the above drawbacks, Ip et al. (2012)[1] and Ecker et al. (2014)[2] presented a supraretinacular ECM (SRECTR) surgery in which an endoscope is inserted superficially to the flexor retinaculum (also known as transverse carpal ligament). This technique improves visualization of carpal tunnel structures and avoids disturbing the median nerve prior to retinaculum dissection as the carpal tunnel is not violated. In Ip et al., the instruments used included a scope sheath, 2 dilators of different sizes and scissors. In Ecker et al., an endoscope, different types of scissors and a speculum are used.

1 Wing-Yuk Josephine Ip, Tamer Ahmed Sweed, Kwok Keung Boris Fung, George L. Tipoe, and Tze Shing Pun (2012) A New Technique of Single Portal Endoscopic Carpal Tunnel Release. Journal of Techniques in Hand & Upper Extremity Surgery, Volume 16, Number 1, March 2012, Pg 27-29

2 J. Ecker, N. Perera and J. Ebert (2014) Supraretinacular endoscopic carpal tunnel release: surgical technique with prospective case series. Journal of Hand Surgery (European Volume) XXE(X) 1-6, 25 Feb. 2014

It has been reported that a high incidence of pillar pain and hypertrophied scars occurred post-operatively among patients. This could be due to the fact that the instruments used in the SRECTR technique were bulky as they were originally designed for cubital tunnel release.

U.S. Pat. No. 5,431,153 disclosed a surgical retractor for exposing the transverse carpal ligament through a small transverse incision along the wrist thereby enabling splitting of the carpal ligament to decompress the carpal tunnel. The surgical retractor comprises essentially of (1) a blade having an arc-shaped configuration in cross section, which becomes progressively flatter towards the tip section and is substantially flat and spade-shaped in plan view, (2) a finger gripping portion projects upwardly from the proximal end of the blade, which is also relatively arc-shaped in cross section and (3) a fiber optic conduit. The arc-shaped configuration provides concave grooves along the finger gripping portion and the blade. The fiber optic conduit runs within the groove to illuminate the surgical cavity formed between the carpal ligament and overlying structures during carpal tunnel release surgery.

In use, a surgeon uses the clearance below the fiber optic conduit in the blade portion to sight, through the incision, along the top of the transverse carpal ligament, the ligament and surrounding nerves, to enable precise cutting of the transverse carpal ligament.

The clearance below the fiber optic conduit in the blade portion is very small and the fiber optic conduit is provided solely for illumination purpose. Hence, it does not provide adequate visual field for a surgeon to see clearly the surgical cavity. Under such condition, it has proven difficult for surgeons to identify the ligament and surrounding nerves to perform the release surgery without complications.

This invention thus aims to alleviate some or all of the problems of the prior art.

SUMMARY OF THE INVENTION

In accordance with an aspect of the invention, there is provided an endoscopic-release surgical retractor comprising a blade having an arch-shaped cross section and a handle extending upwardly from the proximal end of the blade. The handle is adapted to removably receive a L-shaped endoscope-retainer, wherein the vertical arm of the retainer is adapted to receive an endoscope such that in use the endoscope is retained at the apex of the arch.

In an embodiment, the blade may comprise a distal taper with a degree of taper up to 2.5°. The distal-tapered blade may further comprise a profile taper with a degree of taper up to 2.5°.

In another embodiment, the blade may be a non-distal taper. The non-distal-tapered blade may further comprise a profile taper with a degree of taper up to 2.5°.

In yet another embodiment, the blade may have a semi-circular, a stilted or a horseshoe arch-shaped cross section. The length of the blade may range from 4 cm to 6 cm.

According to an embodiment, the handle may include a slot disposed approximate to the proximal end of the blade such that the horizontal arm of the L-shaped endoscope-retainer is receivable within the slot and is secured therein.

The shape of the slot may correspond to the cross section of the horizontal arm such that the L-shaped endoscope-retainer is receivable within the slot.

In a further embodiment, the vertical arm of the L-shaped endoscope-retainer may be provided with an aperture suitably sized and shaped such that an endoscope is receivable and rigidly held therein. The length of the horizontal arm may be greater than or correspond to the length of the vertical arm.

The present invention seeks to overcome the problems of the prior art by providing an endoscopic-release surgical retractor which is safe, easy to use and allows for a less invasive procedure.

When used to relieve carpal tunnel syndrome, the blade of the present invention having an arch-shaped cross section is designed to define a surgical cavity between the flexor retinaculum and the overlying subcutaneous fat and skin for insertion of an endoscope and ligament cutting tools. This avoids the need to insert any instruments into the tight stenotic carpal tunnel to view the carpal tunnel ligament. Hence, it reduces substantially the risk of iatrogenic injury to the median nerve and other adjacent structures.

The design of the surgical retractor of this application advantageously provides excellent visual field to a surgeon for advancing the retractor within the space between the flexor retinaculum and overlying structures. Furthermore, the arch allows entry of an endoscope with different diameters as well as a ligament cutting tool such as a Metzenbaum scissor, surgical blade and laparoscopic scissor.

After inserting the blade of the present invention into the space between the flexor retinaculum and overlying structures, an endoscope is subsequently inserted into the defined surgical cavity through the arch of the blade. The endoscope-retainer is structured and configured to stabilize the insertion of the endoscope through the arch, and to retain the position of the endoscope at the apex of the arch throughout surgery. This advantageously provides for a stable endoscopic visual field throughout the SRECTR surgery and substantially prevents the endoscope from impinging on adjacent structures.

Furthermore, an incision is made transversely along the radiocarpal wrist flexion crease when using the surgical retractor of this application. It advantageously provides rapid healing and excellent scar tissue formation following the SRECTR surgery.

BRIEF DESCRIPTION OF THE DRAWINGS

The invention is illustrated, although not limited, by the following description of embodiments made with reference to the accompanying drawings in which:

FIG. 9 shows an exploded perspective view of the surgical retractor of FIG. 8.

FIG. 10 shows a perspective view of the surgical retractor of FIG. 9 after the endoscope-retainer is attached.

FIG. 11 shows a front view of FIG. 10.

DETAILED DESCRIPTION OF THE EMBODIMENTS

Figures 1A, 1B:
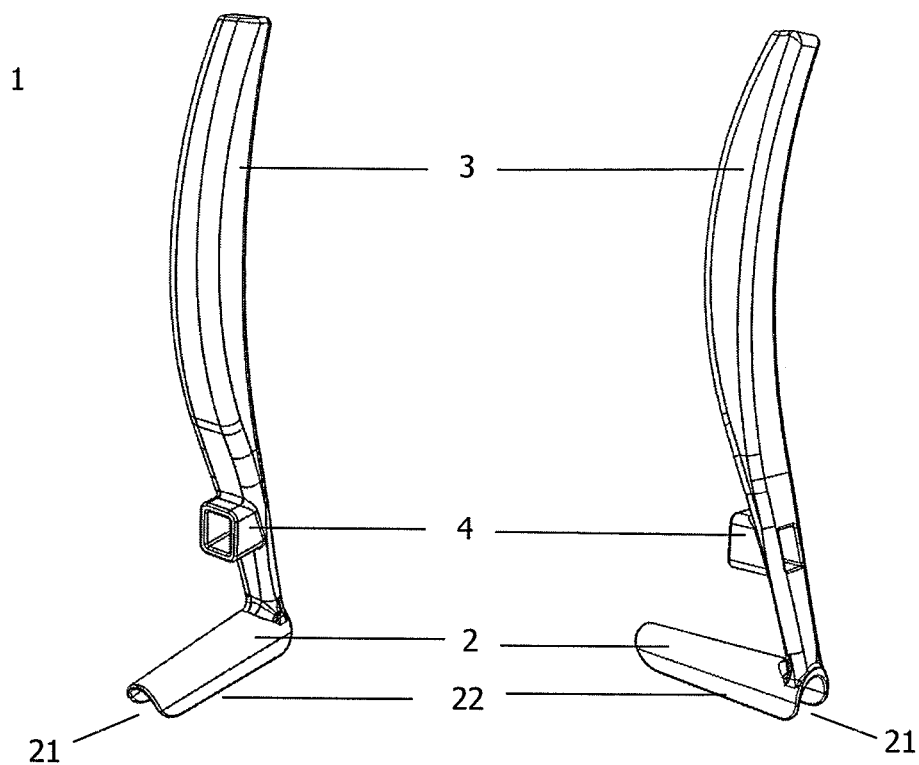
FIGS. 1a to 1d show the perspective views of a distal-tapered blade together with a handle according to a preferred embodiment of the present invention.
Figures 1C, 1D:
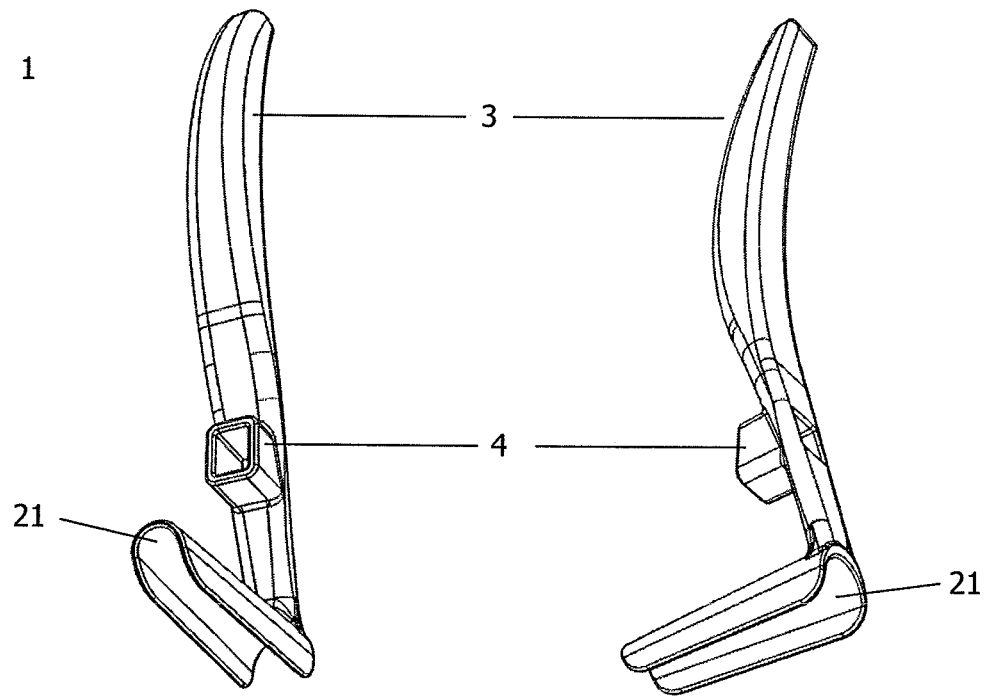

The present invention provides an endoscopic-release surgical retractor 1 suitable for use in release surgery of ligaments, tendons and bones in different parts of the body.

The retractor mainly comprises a blade 2 having an arch-shaped cross section and a handle 3 extending upwardly from the proximal end of the blade 2. The handle is adapted to removably receive a L-shaped endoscope-retainer 5, wherein the vertical arm 52 of the endoscope-retainer is adapted to receive an endoscope such that in use the endoscope is retained at the apex of the arch of the blade.

The blade 2 may be in any suitable configuration and size depending on the type of release surgery, the part of the body which the endoscopic-release surgical retractor is to be used, the size of the patient and the size of the available supraretinacular space (for carpal tunnel release surgery).

Given the above, the blade 2 may have any suitable configuration of arch-shaped cross section, for example a semicircular, a stilted or a horseshoe arch-shaped cross section. The blade is arch-shaped in cross section such that an arch 21 is defined at its ventral face. The arch includes a crown 23 and longitudinal edges 22 disposed substantially parallel to each other. An endoscope and ligament cutting tools are insertable within this arch.

FIGS. 1a to 1d show an embodiment of an endoscopic-release surgical retractor 1 according to the present invention, whereby the blade 2 is a distal taper. In this embodiment, the arch 21 tapers gradually from the proximal end of the blade 2 towards the distal end. The blade 2 may be tapered up to 2.5°, preferably at 1.9°. This results in the width of the arch being greater at its proximal end than its distal end. The width at the proximal end may be ranging from 1.10 cm to 1.20 cm, preferably at 1.20 cm, and the width at the distal end may be ranging from 0.7 cm to 1.2 cm, preferably at 0.9 cm.

FIGS. 4a to 4d show another embodiment of an endoscopic-release surgical retractor 1 according to the present invention, whereby the blade 2 is a non-distal taper. In this embodiment, the arch 21 is uniform in size, namely, the width at the proximal end and distal end of the blade is the same, ranging from 0.7 cm to 1.20 cm.

In any one of the above embodiments, the distal-tapered blade or the non-distal-tapered blade may further include a profile taper. The longitudinal edges 22 of the blade tapers gradually from the proximal end of the blade 2 towards the distal end (FIGS. 3 and 6), with a degree of taper up to 2.5°, preferably at 1.9°. Optionally, the crown 23 of the blade may taper gradually from the proximal end of the blade 2 towards the distal end, with a degree of taper up to 1.5°, preferably 1.3°. This results in the height of the blade being greater at its proximal end than its distal end. The height of the blade 2 at the proximal end may be ranging from 5 mm to 11 mm, preferably at 10.28 mm, and the height at the distal end may be ranging from 3 mm to 11 mm, preferably 8.2 mm.

The blade 2 may be provided in different length configurations ranging from 4 cm to 6 cm. As would be understood by a skilled person, the length depending on the type of release surgery. For example, for SRECTR surgery, the length of the blade 2 is preferably 4.5 cm.

The handle 3 extends upwardly from the proximal end of the blade 3. It may be angled to tilt towards the distal end of the blade 2 by 12.4° to 12.6°, from the vertical.

The handle 3 may be of any suitable configuration that enables gripping by a surgeon such that the endoscopic-release surgical retractor 1 can be easily manipulated as desired during surgery.

Figures 2, 3:
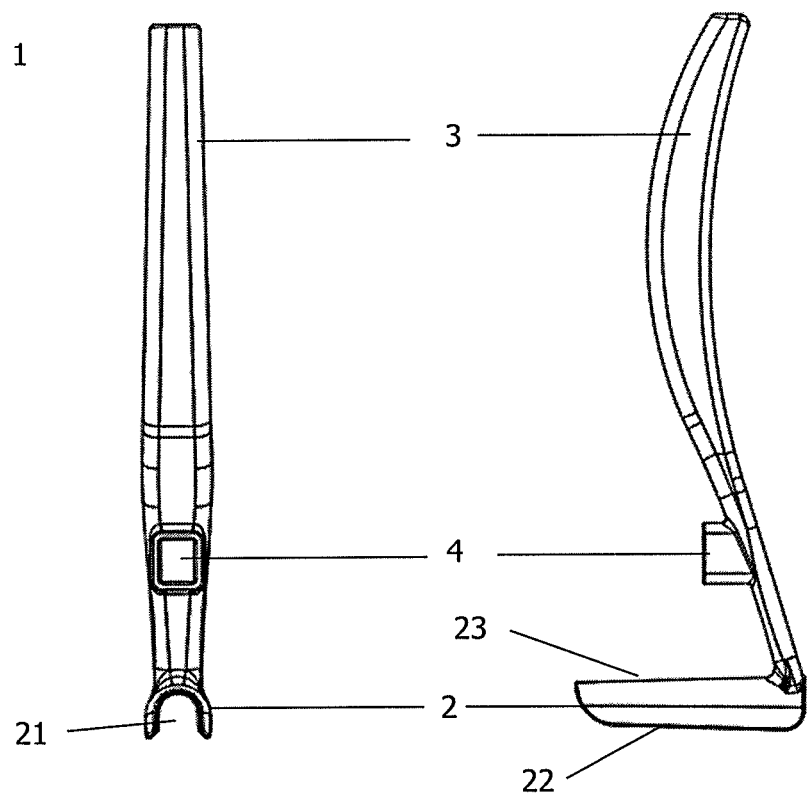
FIG. 2 is a front view of FIGS. 1a to 1d.
FIG. 3 is a side view of FIGS. 1a to 1d.
Figures 4A, 4B:
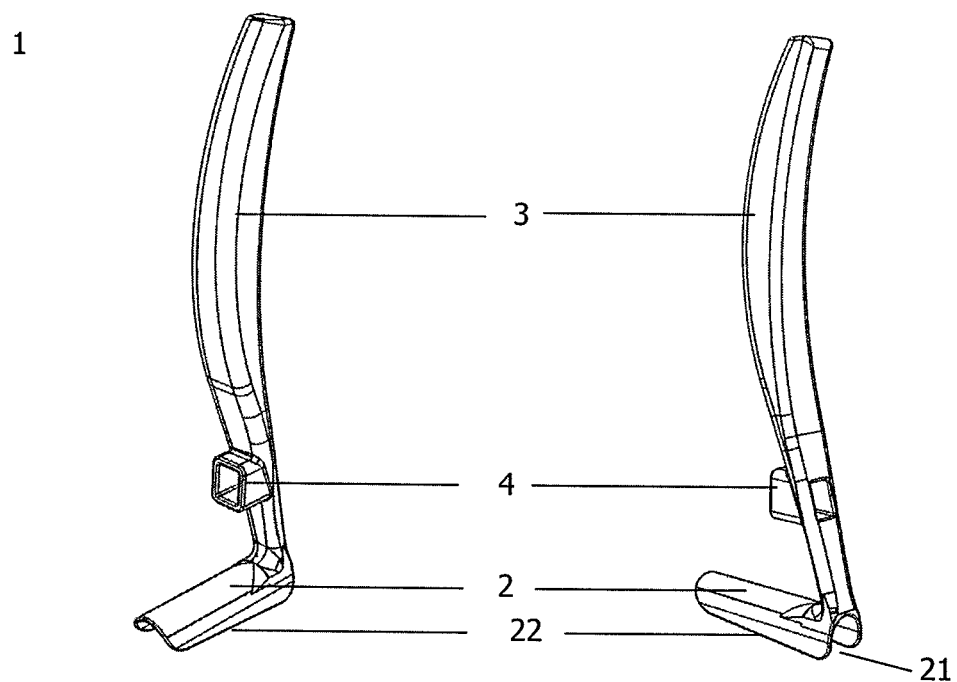
FIGS. 4a to 4d show the perspective views of a non-distal-tapered blade together with a handle according to another embodiment of the present invention.
Figures 4C, 4D:
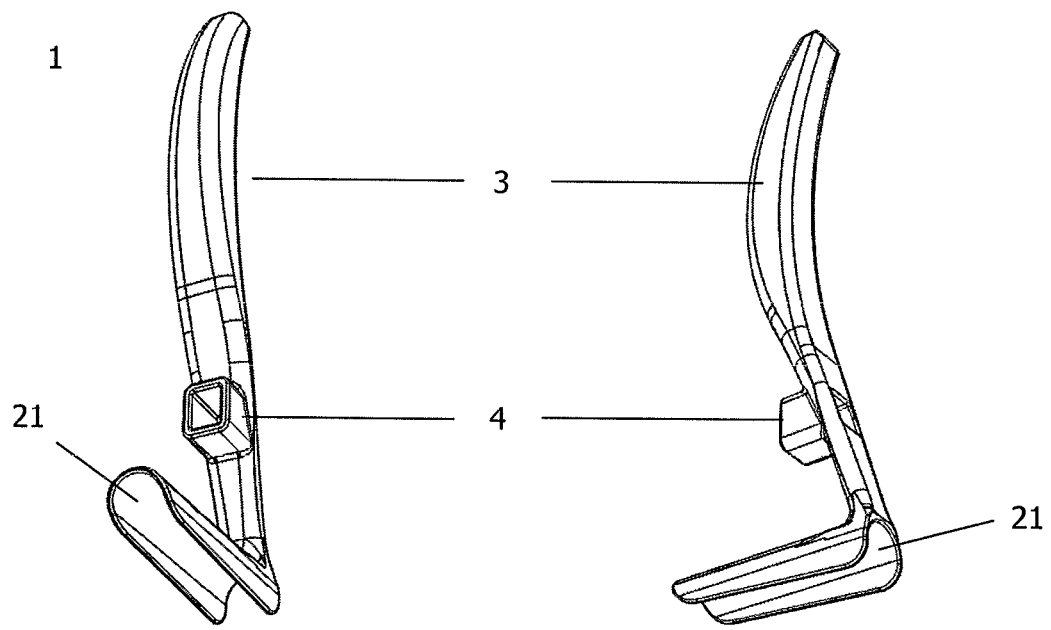
Figures 5, 6:
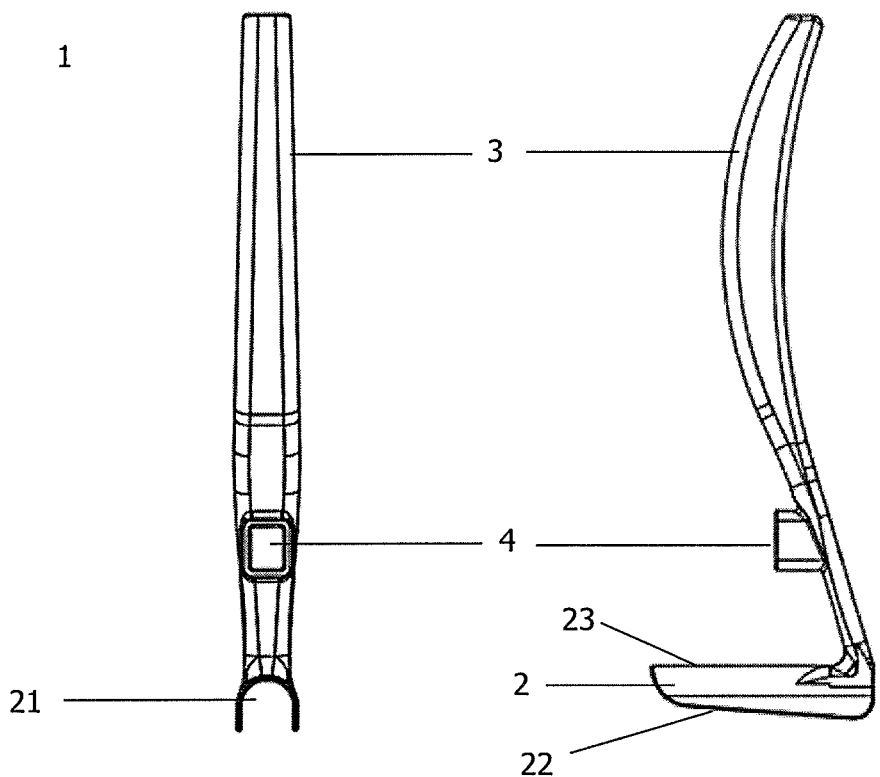
FIG. 5 is a front view of FIGS. 4a to 4d.
FIG. 6 is a side view of FIGS. 4a to 4d.
Figure 8:
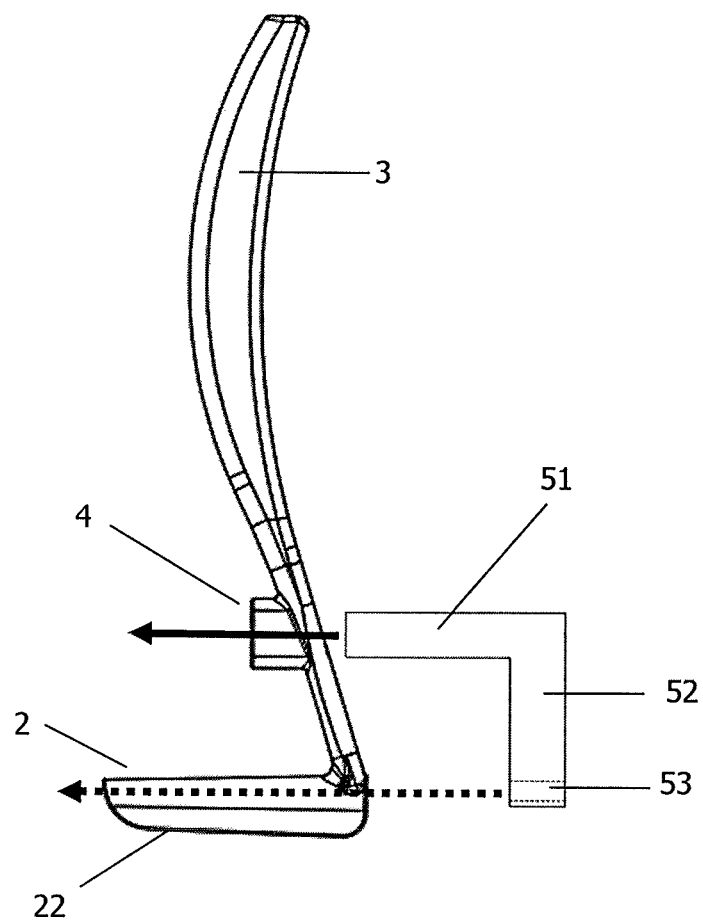
FIG. 8 shows a side view of the surgical retractor before the endoscope-retainer is attached.

Further, the handle 3 is adapted to removably receive a L-shaped endoscope-retainer 5. Any form of adaptation may be employed, provided it allows the endoscope-retainer 5 to be removably attached to the handle 3 and then firmly secured thereat to prevent oscillation of the endoscope-retainer 5 during surgery. This could be realised by way of fastening, stowing, clipping, hooking or mounting. For this purpose, the handle 3 may include a slot 4, disposed approximate to the proximal end of the blade 2 (FIGS. 3 and 6). The slot 4 may be structured in any suitable configuration. In the embodiment of FIG. 8, the slot is a through-hole. Primarily, the through-hole may be of any shape that corresponds to the cross section of the horizontal arm 51 of the endoscope-retainer 5.

The L-shaped endoscope-retainer 5 is provided separate from the endoscopic-release surgical retractor 1 and functions as a support to stabilize and to retain an endoscope in position during surgery.

As denoted by the name, the L-shaped endoscope-retainer 5 comprises a horizontal arm 51 and a vertical arm 52. The dimension of the endoscope-retainer 5 may be varied. The length of the horizontal arm 51 and the vertical arm 52 may be the same or may be different. Furthermore, the horizontal arm 51 and the vertical arm 52 may have a rectangular, square or circular cross section.

In the embodiment of FIGS. 8 and 10, the horizontal arm 51 of the L-shaped endoscope-retainer 5 is inserted into the slot 4 and can be secured rigidly therein so as to prevent oscillation of the endoscope-retainer 5 during surgery.

Figure 7:
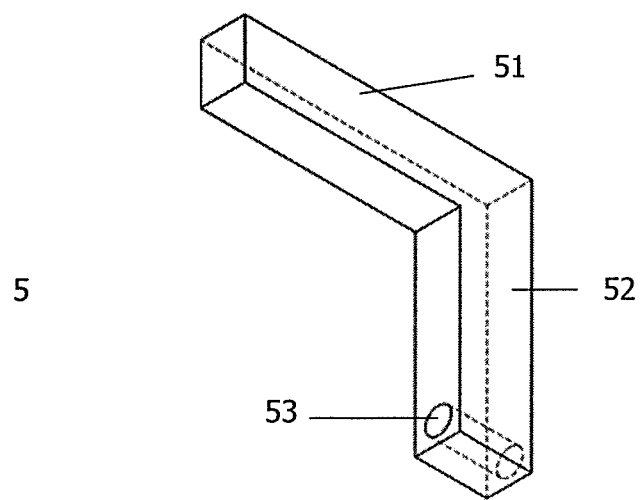
FIG. 7 shows a perspective view of an endoscope-retainer according to an embodiment of the present invention.

The vertical arm 52 of the endoscope-retainer 5 is configured with a structure suitable for receiving and retaining an endoscope at the apex of the arch 21 of the blade 2. For example, the structure may be a dip or clamp or any other configurations that allows insertion of an endoscope into the arch 21 and retains the endoscope at the apex of the arch 21 of the blade 2 once it has reached certain depth within the arch 21. In the embodiment of FIG. 7, an aperture 53 is provided at distal end of the vertical arm 52. In use, when the endoscope-retainer 5 has been attached to the handle 3, the aperture is positioned such that it aligns with the apex of the arch 21 of the blade (FIG. 11). This enables passage of the endoscope through the aperture 53 into the arch of the blade, as shown with the dashed arrow in FIG. 8.

The aperture 53 may be of varying diameter dependent on the type or size of the endoscope used. However, the aperture 53 should be sized to allow passage of an endoscope, but at the same time to retain the endoscope at the apex of the arch of the blade during surgery.

The L-shaped endoscope-retainer 5 may be made of any suitable material which is safe for use in surgery and allows for sterilization (if it is to be re-used). Preferably, the L-shaped endoscope-retainer 5 is made of a surgical stainless steel. However, the L-shaped endoscope-retainer 5 may be disposable. Thus, any suitable medical grade plastic materials may be used.

As mentioned at the beginning of this section, the endoscopic-release surgical retractor 1 of the present invention may be used in release surgery of ligaments, tendons and bones in different parts of the body, for example, carpal tunnel release surgery, plantar fascia release surgery, gastrocnemius release surgery.

The use of the endoscopic-release surgical retractor 1 of this application will now be explained with the example of carpal tunnel release surgery. This in no way limits the scope of the claims, but Is provided herein as an exemplary explanation of the endoscopic-release surgical retractor 1 when in use. The same technique is equally applicable when it is used for other release surgery such as plantar fascia release surgery and gastrocnemius release surgery.

During carpal tunnel release surgery, a transverse incision of about 2 cm is made over the radiocarpal wrist flexion crease, between the palmaris longus tendon and the ulnar border of the ring finger.

Figure 12:
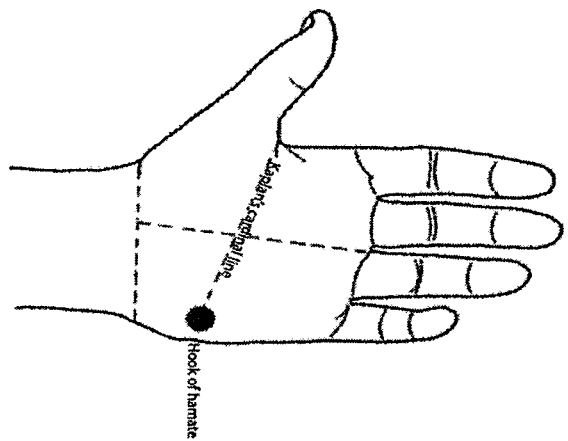
FIG. 12 is a schematic view of a hand of a patient with the labels of Kaplan's cardinal line and the hook of hamate.

A supraretinacular space between the flexor retinaculum and overlying subcutaneous fat and skin is created using a Metzenbaum scissors by blunt dissection along the axial line between the middle and ring finger and ends at the Kaplan's cardinal line as shown in FIG. 12. The width of the supraretinacular space made is about 2 to 3 cm to allow easy insertion of the endoscopic-release surgical retractor 1.

Figure 13:
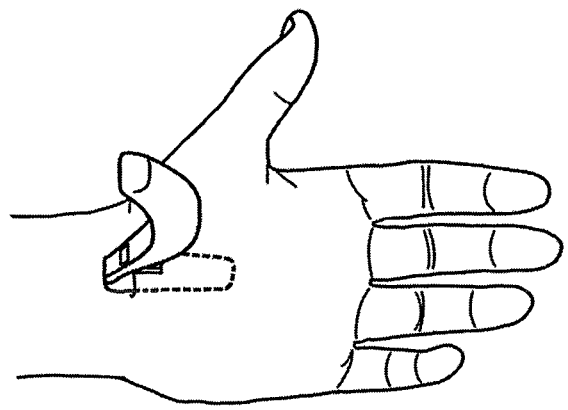
FIG. 13 is a schematic view in which the blade of the surgical retractor of FIG. 1a is inserted into the supraretinacular space through a transverse incision made at the radiocarpal wrist flexion crease.
Figure 14:
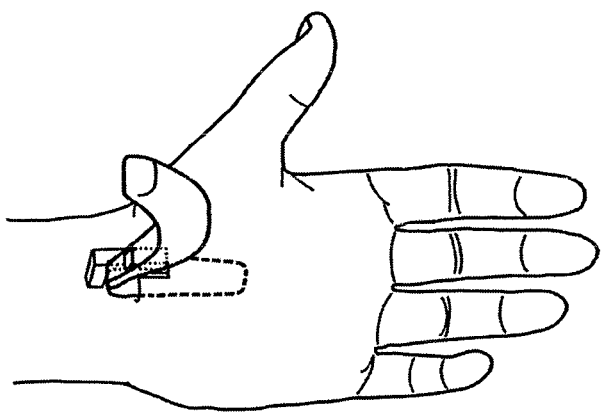
FIG. 14 is a schematic view in which the endoscope-retainer is attached to the handle of the surgical retractor.

With reference to FIGS. 13 and 14, the endoscopic-release surgical retractor 1 is inserted into the supraretinacular space via the transversion incision and the L-shaped endoscope-retainer 5 is subsequently attached to the handle 3.

Figure 15:
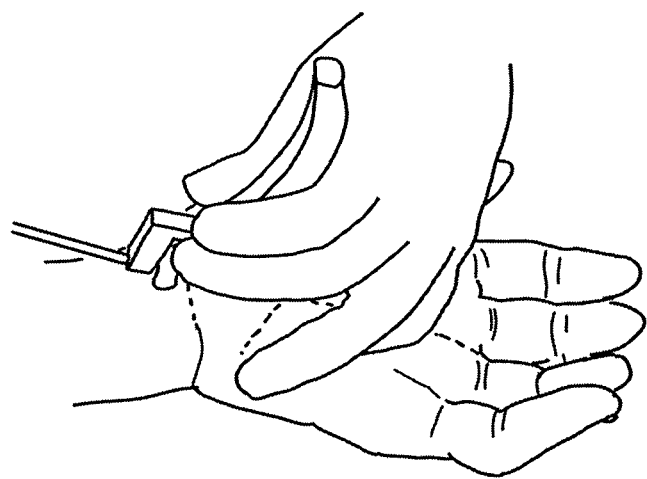
FIG. 15 is a schematic view in which an endoscope is inserted into the arch via the aperture of the endoscope-retainer.
Figure 16:
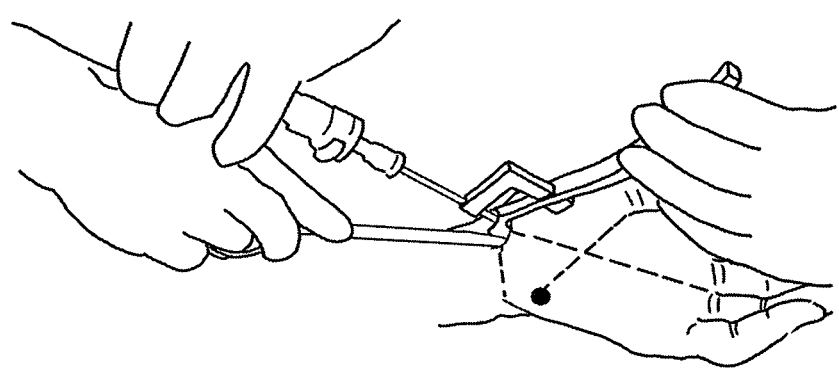
FIG. 16 is a schematic view in which a cutting tool is subsequently inserted into the supraretinacular space via the clearance beneath the endoscope of FIG. 15.

Next, an endoscope is inserted into the arch of the blade via aperture 53 of the endoscope-retainer 5. Due to the firm attachment of the endoscope-retainer 5 to the handle 3 and alignment of the aperture 53, the endoscope is retained rigidly at the apex of the arch. This allows visualization of the entire transverse carpal ligament. Metzenbaum scissors is inserted beneath the L-shaped endoscope-retainer 5 (FIG. 15) to dissect the proximal part of the transverse carpal ligament to visualize the median nerve underneath. The transverse carpal ligament is then divided along the longitudinal axis of the radial border of the ring finger with Metzenbaum scissors under endoscopic vision. This is performed in a series of small sequential cuts, dissecting tissues beneath the transverse carpel ligament to ensure that all structures, especially the median nerve, are not adherent to it before a cut is made. The steps are repeated until the entire transverse carpal ligament is released. Thereafter, the endoscopic-release surgical retractor 1 can be withdrawn through the incision.

All directional statements such as front/forward, back/rear, top, bottom, lateral, inward, outward, made herein are relative to the orientation of the device, in use.

As will be readily apparent to those skilled in the art, the present invention may easily be produced in other specific forms without departing from its scope or essential characteristics. The present embodiments are, therefore, to be considered as merely illustrative and not restrictive, the scope of the invention being indicated by the claims rather than the foregoing description, and all changes which come within therefore intended to be embraced therein.

The invention claimed is:

1. An endoscopic-release surgical system, comprising:
   a retractor (1) including a blade (2) having an arch-shaped cross section and
   a handle (3) extending upwardly from a proximal end of said blade (2); characterized in that
   the endoscopic-release surgical system further comprises a L-shaped endoscopic-retainer (5) having a horizontal arm (51) and a vertical arm (52);
   the handle (3) of the retractor (1) including a through-hole (4) to removably receive and rigidly secure the horizontal arm (51) of the L-shaped endoscope-retainer (5); and
   the vertical arm (52) of said L-shaped endoscopic-retainer including an aperture (53) disposed at its distal end to receive and secure an endoscope such that when the endoscopic-release surgical system is in use, the endoscope is retained at an apex of the arch of the blade (2).

2. The endoscopic-release surgical system according to claim 1, wherein said blade (2) comprises a distal taper with a degree of taper up to 2.5°.

3. The endoscopic-release surgical system according to claim 2, wherein said distal-tapered blade further comprise a profile taper with a degree of taper up to 2.5°.

4. The endoscopic-release surgical system according to claim 1, wherein said blade (2) comprises a non-distal taper.

5. The endoscopic-release surgical system according to claim 4, wherein said non-distal-tapered blade further comprises a profile taper with a degree of taper up to 2.5°.

6. The endoscopic-release surgical system according to claim 1, wherein said blade (2) comprises a semi-circular arch-shaped cross section.

7. The endoscopic-release surgical system according to claim 1, the through-hole (4) of said handle (3) is disposed approximate to the proximal end of said blade (2).

8. The endoscopic-release surgical system according to claim 1, wherein the shape of said through-hole (4) corresponds to the cross section of the horizontal arm (51) such that said L-shaped endoscope-retainer (5) is receivable within said through-hole.

9. The endoscopic-release surgical system according to claim 1, wherein the length of said horizontal arm (51) is greater than the length of said vertical arm (52).

10. The endoscopic-release surgical system according to claim 1, wherein the length of said horizontal arm (51) corresponds to the length of said vertical arm (52).

\* \* \* \* \*